United States Patent
Bechtel et al.

(10) Patent No.: US 11,302,338 B2
(45) Date of Patent: Apr. 12, 2022

(54) RESPONDING TO REQUESTS FOR INFORMATION AND OTHER VERBAL UTTERANCES IN A HEALTHCARE FACILITY

(71) Applicant: CERNER INNOVATION, INC., Kansas City, KS (US)

(72) Inventors: Todd Bechtel, Overland Park, KS (US); Chad Hays, Overland Park, KS (US); Amanda Sleightholm, Kansas City, KS (US)

( * ) Notice: Subject to any disclaimer, the term of this patent is extended or adjusted under 35 U.S.C. 154(b) by 201 days.

(21) Appl. No.: 16/728,923

(22) Filed: Dec. 27, 2019

(65) Prior Publication Data

US 2020/0211573 A1 Jul. 2, 2020

Related U.S. Application Data

(60) Provisional application No. 62/786,886, filed on Dec. 31, 2018.

(51) Int. Cl.
*G10L 15/22* (2006.01)
*G10L 17/24* (2013.01)
(Continued)

(52) U.S. Cl.
CPC ............. *G10L 17/24* (2013.01); *G10L 15/07* (2013.01); *G10L 15/22* (2013.01); *G16H 10/60* (2018.01);
(Continued)

(58) Field of Classification Search
CPC ......... G10L 15/22; G10L 15/08; G10L 15/26; G10L 17/24; G10L 17/00; G10L 13/02; G10L 15/07; G10L 15/1815; G10L 2015/223; G10L 2015/225; G10L 2021/02082; G10L 2021/02166; G10L 21/0232; G10L 21/0272; G10L 25/48; G10L 25/63; G16H 10/60; G16H 40/20; G16H 10/20; G16H 50/20; G16H 70/20; G16H 40/63; G16H 20/40; G16H 50/50;
(Continued)

(56) References Cited

U.S. PATENT DOCUMENTS

6,425,764 B1 * 7/2002 Lamson ................ A61M 21/00
434/236
9,345,404 B2 * 5/2016 Proud ................... A61B 5/0015
(Continued)

*Primary Examiner* — Vijay B Chawan
(74) *Attorney, Agent, or Firm* — Cerner Innovation, Inc.

(57) ABSTRACT

Systems, methods, and devices are provided for responding to requests received from users in a healthcare facility, and for generating alerts based upon criticality detected in received verbal utterances. A personal assistant device (PAD) may receive a verbal request for information. The identity of the requestor may be verified and a response to the request may be received by the PAD. In some cases, prior to audibly outputting the response, it may be determined whether the response contains protected health information (PHI). Upon determining that the response contains PHI, the presence of persons other than the patient in proximity to the PAD and/or security of the location of the PAD may be evaluated prior to audibly outputting the response. Additionally, alerts having a heightened criticality may be generated when a received verbal utterance is determined to have a heightened criticality.

16 Claims, 5 Drawing Sheets

(51) Int. Cl.
  *G10L 15/07* (2013.01)
  *G16H 10/60* (2018.01)

(52) U.S. Cl.
  CPC .. *G10L 2015/223* (2013.01); *G10L 2015/225* (2013.01)

(58) Field of Classification Search
  CPC ........ G16H 30/40; G16H 40/67; G16H 15/00; G16H 20/10; G16H 50/30; G16H 80/00; G16H 20/30; G16H 40/60
  USPC .... 704/246, 235, 270, 270.1, 253, 251, 231, 704/9, 257
  See application file for complete search history.

(56) References Cited

U.S. PATENT DOCUMENTS

| | | | | |
|---|---|---|---|---|
| 9,536,049 | B2* | 1/2017 | Brown | G16H 50/20 |
| 9,704,209 | B2* | 7/2017 | Proud | G06Q 10/10 |
| 10,304,314 | B2* | 5/2019 | Fateh | G16H 40/63 |
| 2009/0089100 | A1* | 4/2009 | Nenov | G16H 10/60 705/3 |
| 2014/0074454 | A1* | 3/2014 | Brown | G10L 15/08 704/9 |
| 2014/0247155 | A1* | 9/2014 | Proud | A61B 5/1118 340/870.16 |
| 2014/0249853 | A1* | 9/2014 | Proud | G06Q 10/10 705/3 |
| 2014/0278506 | A1* | 9/2014 | Rogers | G16H 40/63 705/2 |
| 2015/0120320 | A1* | 4/2015 | Fateh | G16H 20/30 705/2 |
| 2015/0164436 | A1* | 6/2015 | Maron | A61B 5/7282 340/540 |
| 2018/0068082 | A1* | 3/2018 | Brown | G10L 15/22 |
| 2018/0137943 | A1* | 5/2018 | Webb, III | H04L 67/06 |
| 2018/0330626 | A1* | 11/2018 | Donadio | G16H 50/20 |
| 2019/0051415 | A1* | 2/2019 | Owen | A61B 5/7405 |
| 2019/0053706 | A1* | 2/2019 | Martie | A61B 5/0004 |
| 2020/0146638 | A1* | 5/2020 | Wagner | A61B 17/00234 |

* cited by examiner

RESPONDING TO REQUESTS FOR INFORMATION AND OTHER VERBAL UTTERANCES IN A HEALTHCARE FACILITY

CROSS-REFERENCE TO RELATED APPLICATIONS AND PRIORITY CLAIM

This application claims the benefit of U.S. Provisional Patent Application No. 62/786,886, filed Dec. 31, 2018, entitled "Responding To Requests For Information And Other Verbal Utterances In A Healthcare Facility," the entire contents of which is incorporated herein by reference.

BACKGROUND

On a typical shift, members of a patient's healthcare team generally are attending to a number of patients, as well as performing other tasks such as documenting actions in patient charts, consulting with other healthcare team members, counseling patients' loved ones, and the like. As such, a patient present in a location of a healthcare facility (for instance, a hospital room or a clinical care office examination room) encounters periods of time in which a member of her healthcare team is not present in the location with the patient. By way of example, during an in-patient hospital stay, a patient may encounter lengthy periods of time during which she is monitored by one or more medical devices but not directly observed by a member of her healthcare team. In another example, during an out-patient visit to a clinician's office, a patient may encounter periods of time during which she is waiting in an examination room for the clinician to join her. During times such as these, the patient may desire information pertaining to her conditions, medications, diagnoses, care, etc.; information that generally may be readily available in association with her clinical records stored in association with an electronic healthcare information system (EHIS). However, even if the patient is permitted access to her complete clinical records, she may not know how to locate the desired information in the records. Further, the patient may be unable to query his or her clinical records via input through a traditional computing interface because, for instance, the patient may be recovering from a procedure and may be unable to physically engage with a keyboard, mouse, etc. Further, during periods of time in which a member of her healthcare team is not present in the location with the patient, she may require additional assistance, the criticality of which may vary greatly.

For reasons such as this, locations within a healthcare facility (e.g., hospital, clinical office examination room, or the like) may include a means for the patient to let a healthcare team member know that assistance is desired. Such means may include a button or switch that may be activated by the patient that illuminates a light outside of the room to indicate the desire for assistance. In other cases, the means for letting a healthcare team member know that assistance is required or desired may include means that permit the patient to open an audio channel between a device in the room (e.g., via a telephone or two-way speaker) and a device at a central healthcare team member location (e.g., a nursing station) or a device specific to a particular healthcare team member. While such solutions may be adequate for informing a healthcare team member of the desire for assistance, if the patient merely desires information she could attain from his or her clinical records without engaging a healthcare team member, such would be preferable so as to not unnecessarily take time and attention away from the healthcare team member. Further, such solutions often fail to convey adequate information to inform the healthcare team member of the criticality of the patient's need.

SUMMARY

The present technology generally relates to devices, systems, and methods for responding to patient requests for information in a healthcare facility. In some cases, a personal assistant device may be utilized. In some cases, a personal assistant device may recognize voice commands making it easier for patients (and/or their proxies) to request information and/or express a need for assistance.

In brief, and at a high level, the present disclosure describes technology that may utilize a personal assistant device (e.g., an AMAZON ECHO or a GOOGLE HOME device) associated with a location in a healthcare facility to receive verbal requests for information and, where appropriate conditions exist, to audibly output responses to such requests. A personal assistant device may receive from a user, via a listening component thereof, a verbal request for information about a patient. The user may be a patient or a proxy authorized to submit requests on behalf of the patient and/or receive responses to submitted requests on behalf of the patient. The identity of the user may be verified (e.g., via a voice signature) and the received verbal request for information may be transmitted to an electronic healthcare information system (EHIS). Clinical records associated with the patient stored in association with the EHIS may be queried for an appropriate response to the verbal information request and the response may be transmitted to and received by the personal assistant device. The response to the verbal information request may be audibly output, via the speaker of the personal assistant device. In some cases, prior to audibly outputting the response to the verbal information request, it may be determined whether or not the response contains protected health information (PHI). If it is determined that the response does not contain PHI, the response may be audibly output without further required action. If, however, it is determined that the response does contain PHI, the presence of persons other than the patient in proximity to the personal assistant device and/or security of the location of the personal assistant device may be evaluated prior to audibly outputting the response.

In this way, healthcare team members may not need to be unnecessarily involved in addressing requests for information when patients are able to readily access the desired information without healthcare team member involvement. Additionally, privacy concerns that may arise due to the audible outputting of PHI can be addressed and alternate means of communicating responses to information requests may be provided where appropriate.

One aspect of the present technology that may accomplish these objectives is a system for responding to requests for information in a healthcare facility. The system may include a personal assistant device associated with a patient and having a listening component and a speaker, the personal assistant device being configured to receive verbal requests for information from a user and to audibly provide responses to received verbal requests. The system further may include a processor in communication with the personal assistant device and an EHIS. Still further, the system may include one or more computer-readable media storing computer-readable instructions that, when executed by the processor, cause the processor to: receive, via the listening component, a verbal request for information from the user, verify an identity of the user, responsive to verifying the identity of the user, transmit the received verbal request for information to the EHIS, receive, from the EHIS, a response to the verbal request for information, and audibly output, via the speaker, the response to the verbal request for information. In some instances, the identity of the user may be verified by detecting a voice signature of the user, comparing the voice signature of the user to one or more voice signatures associated, in the EHIS, with the patient as belonging to the patient or an authorized proxy of the patient, and determining the voice signature belongs to the patient or the authorized proxy of the patient. In some instances, the identity of the user further may be verified by comparing one or more of (1) a location of the personal assistant device associated with the patient, (2) a personal identification number associated with the user, (3) a password associated with the user, (4) a biometric-recognition profile of the user, (5) a location of the user received from a device associated with the user and enabled with a real-time location system, and (6) input of an identification credential associated with the user to information associated with the patient in the electronic healthcare information system.

Another aspect of the present technology that may accomplish these objectives is a system for responding to requests for information in a healthcare facility. The system may include a personal assistant device associated with a patient and having a listening component and a speaker, the personal assistant device being configured to receive verbal requests for information from a user and to audibly provide responses to received information requests. The system further may include a processor in communication with the personal assistant device and an EHIS. Still further, the system may include one or more computer-readable media storing computer-readable instructions that, when executed by the processor, cause the processor to: receive, via the listening component, a verbal request for information from the user; verify an identity of the user; responsive to verifying the identity of the user, transmit the received verbal request for information to the EHIS; receive, from the EHIS, a response to the verbal request for information; determine that the response to the verbal request for information contains protected health information; responsive to determining that the response to the verbal request for information contains protected health information, determine if any persons other than the patient are in proximity to the personal assistant device; and responsive to determining that no persons other than the patient are in proximity to the personal assistant device, audibly output, via the speaker, the response to the verbal request for information. In some cases, responsive to determining that at least one person other than the patient is in proximity to the personal assistant device, an alternate response to the verbal request for information (that is, a response that does not contain PHI) may be audibly output. In some cases, responsive to determining that at least one person other than the patient is in proximity to the personal assistant device, a textual response to the verbal request for information may be output in association with a device, other than the personal assistant device, that is associated with the patient. In some cases, responsive to determining that at least one person other than the patient is in proximity to the personal assistant device, an identity of the at least on other person may be verified as an identity of an individual authorized to receive the PHI of the patient prior to audibly outputting the response to the verbal information request. In some cases, the system further may determine that the location of the personal assistant device is secure (e.g., all doors and windows into a hospital room containing the personal assistant device are closed) prior to audibly outputting the response to the verbal information request.

The present technology further relates to systems, methods and devices for generating alerts for healthcare team members that are indicative of and/or commensurate with the criticality of a verbal utterance. In some cases, a personal assistant device may recognize words, phrases and/or intonations of users' verbal utterances, and/or a facial expression or gesture of a user when speaking a verbal utterance, and generate appropriate alerts in response thereto. In this way, healthcare team members may be able to appropriately prioritize patient requests for assistance with other requests and within the healthcare team member's workflow.

One aspect of the present technology that may accomplish these objectives is a method for responding to verbal utterances in a healthcare facility. The method may include receiving a verbal utterance from a user. In some cases, such verbal utterance may be received via a listening component of a personal assistant device associated with a patient, the personal assistant device being configured to receive verbal utterances from users and to generate alerts responsive to received verbal utterances. The method further may include determining a level of criticality of a received verbal utterance and, responsive to determining the level of criticality of the received verbal utterance, generating an alert. In some cases, the level of criticality of the received verbal utterance may be determined based upon at least one of words contained in the received verbal utterance, phrases contained in the received verbal utterance, intonation of the received verbal utterance, and recognition of a facial expression and/or a gesture of the user upon speaking the received verbal utterance. In some cases, the generated alert is indicative of or commensurate with the level of criticality of the verbal utterance. The method further may include transmitting the generated alert to at least one member of a healthcare team associated with the patient.

Additional objects, advantages, and novel features of the technology are described below in the Detailed Description. They will, in part, become apparent to those skilled in the art, or they may be learned by practice of the technology.

BRIEF DESCRIPTION OF THE DRAWINGS

The present technology is described in the Detailed Description with reference to the attached figures, wherein.

DETAILED DESCRIPTION

The subject matter of the present technology is described herein with specificity to meet statutory requirements. However, the description itself is not intended to limit the scope of this disclosure. Rather, the inventors have contemplated that the claimed subject matter also might be embodied in other ways, to include different steps or combinations of steps similar to the ones described in this document, in conjunction with other present or future technologies. Moreover, although the term "step" may be used herein to connote different elements of methods employed, the term should not be interpreted as implying any particular order among or between various steps disclosed, unless the order of individual steps is explicitly described.

Embodiments of the present technology are directed to methods, systems, and computer-readable media for utilizing personal assistant devices to respond to requests for information and generate alerts responsive to verbal utterances in a healthcare facility. Certain aspects may provide for audibly outputting responses to verbal requests for information. Certain aspects may provide for audibly outputting responses to verbal requests for information subsequent to verifying the identity of the requestor. Certain aspects may provide for audibly outputting responses to verbal requests for information subsequent to determining the presence and/or identity of persons other than the patient in proximity to the personal assistant device. Certain aspects may provide for audibly outputting responses to verbal requests for information subsequent to determining that a location of the personal assistant device is secure. Certain aspects may provide for determining the criticality of verbal utterances spoken within a healthcare facility. Certain aspects may provide for generating alerts having a criticality indicative of or commensurate with the criticality of received verbal utterances. Further aspects and embodiments are described in detail below.

Figure 1:
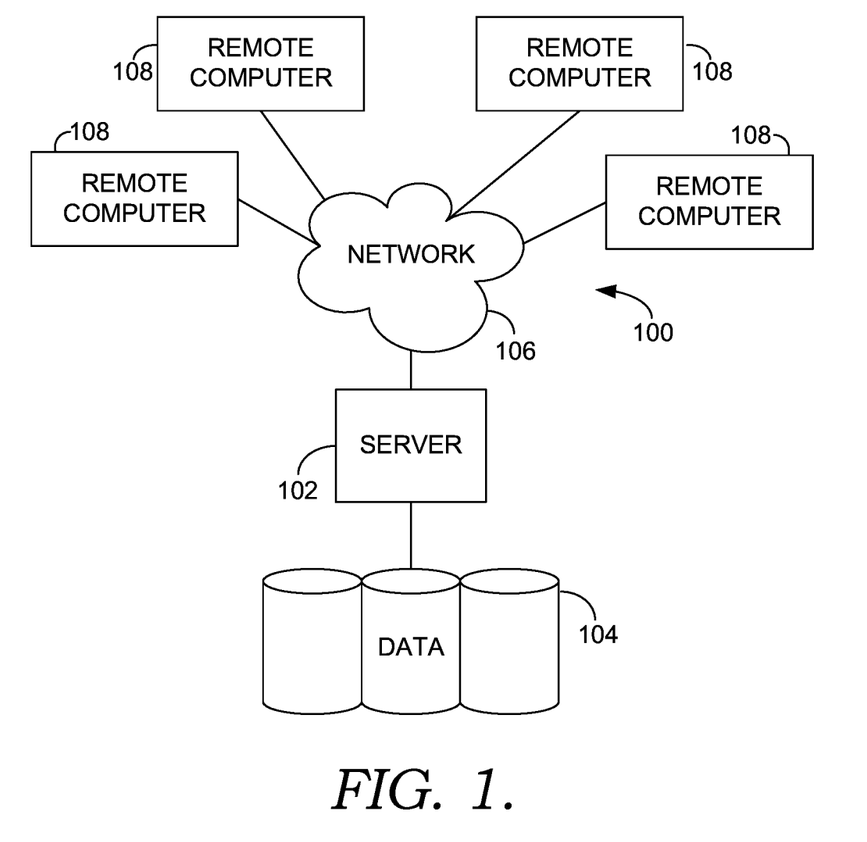
FIG. 1 is a block diagram of an exemplary computing environment suitable for implementing aspects of the described technology, in accordance with embodiments of the present disclosure.

With reference now to FIG. 1, an exemplary computing environment suitable for use in implementing aspects of the technology is described below. An exemplary computing environment (e.g., a medical-information computing-system environment) with which embodiments may be implemented is provided. The computing environment is merely an example of one suitable computing environment and is not intended to suggest any limitation as to the scope of use or functionality of the technology. Neither should the computing environment be interpreted as having any dependency or requirement relating to any single component or combination of components illustrated therein.

The present technology may be operational with numerous other general or special purpose computing system environments or configurations. Examples of well-known computing systems, environments, and/or configurations that may be suitable for use with aspects of the present technology include personal computers, server computers, hand-held or laptop devices, multiprocessor systems, microprocessor-based systems, set top boxes, programmable consumer electronics, network PCs, minicomputers, mainframe computers, personal assistant devices, distributed computing environments that include any of the above-mentioned systems or devices, and the like.

The present technology may be described in the general context of computer-executable instructions, such as program modules, being executed by a computer. Exemplary program modules include routines, programs, objects, components, and data structures that perform particular tasks or implement particular abstract data types. The present technology may be practiced in distributed computing environments where tasks are performed by remote processing devices that are linked through a communications network. In a distributed computing environment, program modules may be located in association with local and/or remote computer storage media (e.g., memory storage devices).

The computing environment comprises a computing device in the form of a control server 102. Exemplary components of the control server 102 comprise a processing unit, internal system memory, and a suitable system bus for coupling various system components, including data stores, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The control server 102 typically includes, or has access to, a variety of non-transitory computer-readable media. Computer-readable media can be any available media that may be accessed by the control server 102, and includes volatile and non-volatile media, as well as, removable and non-removable media. By way of example, and not limitation, computer-readable media may comprise computer storage media and communication media. Computer storage media includes volatile, non-volatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the control server 102. Computer-readable media does not include signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above also should be included within the scope of computer-readable media.

The control server 102 may operate in a computer network using logical connections to one or more remote computers 108. The remote computers 108 may be located at a variety of locations including operating systems, device drivers and medical information workflows. The remote computers also may be physically located in traditional and nontraditional medical care environments so that the entire healthcare community may be capable of integration on the network. The remote computers might be personal computers, servers, routers, network PCs, peer devices, other common network nodes, or the like and might comprise some or all of the elements described above in relation to the control server 102. The devices can be personal digital assistants or other like devices.

The computer network 106 may comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof may be stored in association with the control server 102, the data store 104, or any of the remote computers 108. For example, various application programs may reside on the memory associated with any one or more of the remote computers 108. It will be understood and appreciated by those of ordinary skill in the art that the network connections shown are exemplary and other means of establishing a communications link between the computers (e.g., the control server 102 and the remote computers 108) may be utilized.

In operation, an organization may enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information also may be sent directly from a remote healthcare device to the control server 102. In addition to a monitor, the control server 102 and/or the remote computers 108 may comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
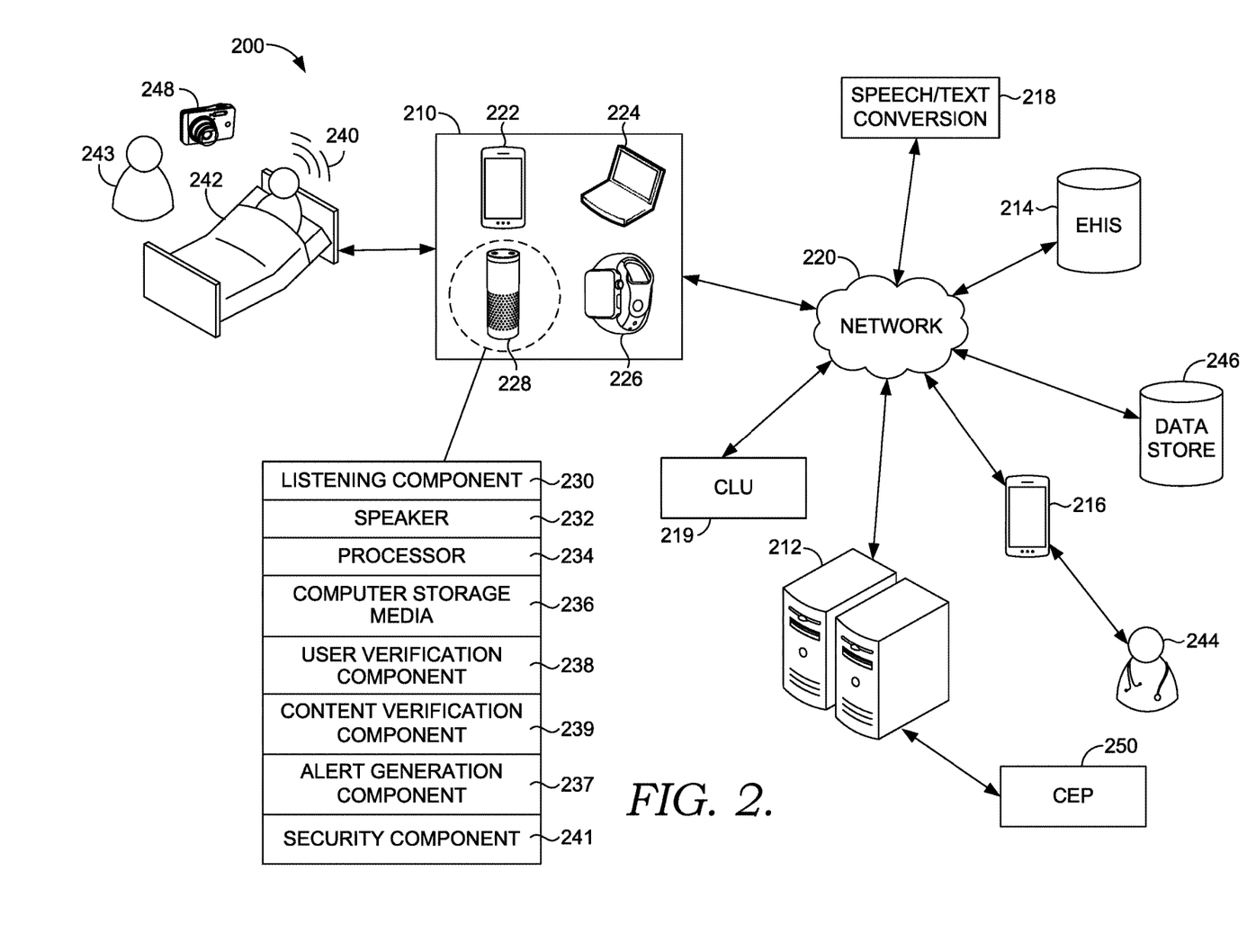
FIG. 2 is a block diagram of an exemplary system for responding to requests for information and other verbal utterances in a healthcare facility, in accordance with embodiments of the present disclosure.

Turning now to FIG. 2, illustrated is a block diagram of an exemplary system 200 for utilizing personal assistant devices to respond to requests for information and generate alerts to verbal utterances in a healthcare facility. In the illustrated aspect, the system comprises one or more patient communication devices 210, a control component 212, an Electronic Healthcare Information System (EHIS) 214, a healthcare team member device 216, a speech/text conversion component 218, and a complex language understanding engine (CLU) 219 all in communication with one another through a network 220. The network 220 may be any type of communication scheme that allows devices to exchange data. For example, the network 220 may include fiber optic, wired and/or wireless communication capability in any of a plurality of protocols, such as TCP/IP, Ethernet, WAP, IEEE 802.11, or any other protocols. Implementations are contemplated in which the system 200 may be accessible through a shared public infrastructure (e.g., the Internet), an extranet, an intranet, a virtual private network (VPN), a local area network (LAN), a wide area network (WAN), a peer-to-peer (P2P) network, a wireless communications network, a telephone network, a facsimile network, a cloud network, or any combination thereof. Such networks are commonplace in today's computing environments and, accordingly, are not further described herein. Although many of the components illustrated in FIG. 2 are described as individual components or functional entities, in some cases, they may be implemented as discrete or distributed components, or in conjunction with other components, having any suitable location or combination.

The system 200 includes one or more patient communication devices 210. The patient communication devices 210 may include devices such as a mobile phone 222 or a user computing device 224. The patient communication device 210 may include other types of mobile devices, such as a tablet, or wearables, such as a wearable device 226, in accordance with aspects of the present technology. In some aspects, the patient communication devices 210 may include a personal assistant device 228. Personal assistant devices are a category of smart speakers that enable users to speak verbal commands, requests, and/or utterances to interact with a personal assistant service that aids the user in obtaining answers to questions and/or in completing certain tasks. Exemplary personal assistant devices include, without limitation, AMAZON ECHO which utilizes a personal assistant service referred to as "Alexa" and GOOGLE HOME, which utilizes a personal assistant service referred to as "Google Assistant." As illustrated, the personal assistant device 228 includes a listening component 230, a speaker 232, a processor 234, computer storage media 236, a user verification component 238, a content verification component 239, an alert generation component 237, and a security component 241. The listening component 230 may be configured for detecting an audible signal 240, for example a verbal request for information from a user (e.g., a patient-user 242, a proxy 243 of a patient-user and/or a healthcare-team-member-user 244) associated with a location in a healthcare facility. Another exemplary audible signal 240 the listening component 230 may be configured for detecting is a verbal utterance spoken by a user. One common example of a type of listening component 230 is a microphone. In some aspects (not shown), the listening component 230 may be a separate component that is communicatively coupled, for example, by hardwire or wirelessly, to the personal assistant device 228.

In general, any person could be considered a user of the system 200. In a non-limiting example, the user may be a patient 242 or a proxy 243 of a patient (that is, a person the patient 242 has designated to speak on his or her behalf and to receive responses to spoken requests on his or her behalf) present in a location of a healthcare facility (for instance, a hospital room or a clinical care office examination room). In another non-limiting example, the user may be a healthcare-team-member-user 244.

In some cases, the audible signal 240 may be a verbal utterance, such as a verbal utterance indicating that the patient-user 242 requires assistance from an appropriate healthcare team member (e.g., healthcare-team-member-user 244). In some cases, the audible signal 240 may be a request for information, for instance, information stored in association with a patient's clinical medical records and the EHIS 214. In some aspects, the audible signal 240 may be in the form of a question.

In some aspects, initial utterance of the audible signal 240 may include a "wake word," that is, a word that alerts the personal assistant device 228 that the user 242, 243 or 244 is speaking a voice command intended for the personal assistant device 228. By way of non-limiting example, the wake word generally utilized with the AMAZON ECHO personal assistant device is "Alexa" and the wake word generally utilized with the GOOGLE HOME personal assistant device is "Google." In a non-limiting example, after the wake word signals the personal assistant device 228 that a request intended for the device is to follow, the user (e.g., the patient-user 242, the proxy 243 of the patient-user, or the healthcare-team-member-user 244) may speak an utterance (e.g., a statement) to invoke their intent. As used in this context, an "intent" represents an action that fulfills the user's spoken request.

By way of example, assume the patient-user 242 is utilizing an AMAZON ECHO personal assistant device and that she desires to utilize the personal assistant device 228 to request information about his or her care from her electronic clinical records stored in association with the EHIS 214. The patient-user 242 in this instance may speak one of a number of utterances that the personal assistant device is programmed to recognize as associated with a "NeedsInformation" intent. For instance, the user may in this instance utter "What medications am I taking?" or "What is my diagnosis?" In some instances, intents can have "slots" that the user may customize to request fulfillment of a particular request. For instance, utilizing the above example, the user 202 may utter "What is my {Item}?" In this instance, the user would speak the name of the desired item in the "slot" indicated as {Item}. The user may utilize a similar spoken format to fulfill other intents as well.

The speaker 232 of the personal assistant device 228 may be configured to provide audible output to the user (e.g., the patient-user 242, the proxy 243 of the patient-user 242 or the healthcare-team-member-user 244). By way of example, the speaker 232 may provide an indication of a response to a request for information or a verbal utterance received by the listening component 230 of the personal assistant device 228. For instance, if the personal assistant device 228 is an AMAZON ECHO device, the patient-user 242 may speak the exemplary voice command "Alexa, what medications am I taking?" Once the appropriate information has been extracted from the EHIS 214, the speaker 232 may audibly output a message to the patient-user 242, for instance, the speaker 232 may audibly output the message "You are taking the following medications:" followed by a list of the patient's current medications. By way of another example, the speaker 232 may audibly output the message "I see only [your designated proxies] are in the room with you. Here is your requested information:" followed by a list of the patient's current medications. The latter exemplary response illustrates cooperation with one or both of the camera 248 and the content verification component 239 of the personal assistant device 228, as more fully described below. Alternatively, the speaker 232 may audibly output an alternate message, for instance, a message void of personal health information of the user, if appropriate (as more fully described below). By way of example, under appropriate circumstances, the speaker 232 may output the alternate message "I see there are other people in the room, let me ask your nurse to get you that information," or "I see your nurse is in the room, he/she can provide you that information." Such alternate responses illustrate cooperation with one or both of the camera 248 and the content verification component 239 of the personal assistant device 228, as more fully described below. In some aspects (not shown), the speaker 232 may be a component separate from the personal assistant device 228 that is communicatively coupled, for example, by hardwire or wirelessly, to the personal assistant device 228.

In some aspects, a verbal request for information may require information in addition to the wake word in order to appropriately route (as more fully described below) the user's request. For instance, the verbal request for information may require information associated with the EHIS 214 in order to be appropriately routed. By way of example, the patient-user 242 may utter the voice command "Alexa, ask my electronic clinical records what medications I am taking." In such an instance, the utterance of "my electronic clinical records" alerts the personal assistance device service where the request for information is to be routed such that the system 200 may query the EHIS 214 for such information.

In some exemplary aspects, the speaker 232 may be configured to prompt the user (e.g., the patient-user 242, the proxy 243 of the patient, or the healthcare-team-member-user 244) for more information or convey to the user that a received request for information is invalid.

The processor 234 of the personal assistant device 228 may be any type of hardware programmed to perform the functions described herein below. For instance, in some embodiments, the processor 234 is a general purpose processor executing instructions stored in memory (not shown). In other embodiments, the processor 234 comprises a special purpose logic component. For example, and without limitation, illustrative types of special purpose logic components that can be used include Field Programmable Gate Arrays (FPGAs), Application-Specific Integrated Circuits (ASICs), Application-specific Standard Products (ASSPs), System-On-a-Chip (SOCs), Complex Programmable Logic Devices (CPLDs), and the like.

Other components of the personal assistant device 228, such as the computer storage media 236 may be similar to those described with respect to the exemplary computing environment of FIG. 1.

The processor 234 and the computer storage media 236 generally operate to route received audible signals 240 (e.g., verbal requests for information and/or verbal utterances) to the appropriate healthcare team member device 216 and/or the EHIS 214. In some cases, the processor 234 and the computer storage media 236 operate to route received audible signals 240 to the speech/text conversion component 218 such that text responses rather than (or in addition to) verbal responses may be routed to the appropriate healthcare team member device 216 and/or the EHIS 214. The processor 234 and the computer storage media 236 further generally operate to route received responses to requests for information to the personal assistant device 228 where the same may be audibly output by the speaker 232 thereof. In some cases, the processor 234 and the computer storage media 236 operate to route received responses to requests for information to the speech/text conversion component 218 such that text responses rather than (or in addition to) verbal responses may be output. In exemplary embodiments, such text responses may be output via a device other than personal assistant device 228, for instance, via a mobile phone 222, a user computing device 224, and/or a wearable device 226. Appropriate conditions for such alternate routing are more fully described below.

Aspects of the present technology contemplate utilizing a personal assistant device (e.g., the personal assistant device 228) to output information through the speaker 232. The Health Insurance Portability and Accountability Act of 1996 (HIPAA) includes a Privacy Rule (The Standards for Privacy of Individually Identifiable Healthcare Information) that protects the disclosure of individuals' "protected health information." To facilitate compliance with the HIPAA Privacy Rule, and to otherwise protect sensitive information associated with a patient-user 242, the personal assistant device 228 may further include a user verification component 238. The user verification component 238 may be configured to verify the identity of a particular user, for instance, the patient-user 242, a proxy 243 of the patient and/or the healthcare-team-member-user 244, upon receipt of a request for information and/or before audibly outputting (e.g., via the speaker 232) any sensitive and/or protected health information. By way of example only, a particular user's identity may be verified by voice and/or by authorization code. For instance, a particular user has a distinct voice signature that may be pre-associated with the particular user in a data store, for example, the data store 246 or a data store associated with the EHIS 214 (not shown). When the listening component 230 of the personal assistant device 228 detects the distinct voice signature, the user verification component 238 may associate the voice signature with the particular user, thereby, verifying the particular user. In another case, verification may be performed using an authorization code, such as a password or PIN number. The code may be predetermined and stored in association with a particular user (e.g., in the data store 246 or in a data store (not shown) associated with the EHIS 214). When the listening component 230 of the personal assistant device 228 detects the code, the user verification component 238 may associate the code with the particular user to verify the user. It will be understood and appreciated by those having ordinary skill in the art that other means of verifying a user's identity are available and are continually being developed. Any and all such existing and future means of user verification are contemplated to be within the scope of aspects of the present technology. In some aspects (not shown), the user verification component 238 may be a component separate from the personal assistant device 228 that is communicatively coupled, for example, by hardwire or wirelessly, to the user verification component 238.

The personal assistant device 228 further includes a content verification component 239 configured to determine whether or not a response to a received request for information includes PHI. In embodiments, rules and algorithms designed to facilitate determination of information as PHI may be employed by the CEP 250 which may aid the content verification component 239 in making the appropriate determination. Responsive to determining that a response to a received request for information does include PHI, the content verification component 239 further may be configured to determine whether any persons other than the patient 242 are in proximity to the personal assistant device 228 prior to the speaker 232 audibly outputting the response. In embodiments, determining whether or not persons other than the patient are in proximity to the personal assistant device 228 may be accomplished in association with a camera 248 in proximity to the location of the personal assistant device. In embodiments, if a person other than the patient is detected in a field-of-view of the camera 248, the content verification component 239 may initiate additional actions (e.g., verification of an identity of the other persons or the like) prior to audibly outputting the response to the request for information. In some embodiments, the camera 248 may include three-dimensional image capabilities.

The personal assistant device 228 further includes a security component 241. The security component 241 may be configured to determine whether a location of the personal assistant device 228 is secure prior to the speaker 232 audibly outputting a response to a request for information when the response is determined to contain PHI. In embodiments, the location of the personal assistant device 228 may be determined to be secure when all doors and windows into the location of the personal assistant device 228 are securely closed.

With continued reference to FIG. 2, the system 200 includes a control component 212. The control component 212 may be configured to determine appropriate routing for received requests/responses. For instance, the control component 212 may be configured to receive requests for information (e.g., from the personal assistant device 228), receive responses to requests for information (e.g., from the EHIS 214) and appropriately route such requests and responses. In embodiments, requests for assistance and responses thereto may be received by the control component 212 as audio files and/or as text files. By way of example, the control component 212 may be configured to receive an audio file request from the patient 242, determine that the received request is to be routed as an audio file to the speech/text conversion component 218 for conversion from the audio file to a text file and then to the EHIS for querying against the electronic clinical records associated with the patient 242. In another instance, the control component 212 may determine that a text file response to a patient request for information is to be routed to the speech/text conversion component 218 for conversion from text to speech and subsequently to the personal assistant device 228 associated with the patient from whom the request for information was received for outputting by the speaker 232. In this instance, the control component 212 further may determine that the text file is to be routed to the EHIS 214 for storage.

The control component 212 further may be communicatively coupled with a complex event processing platform (CEP) 250. The CEP 250 may be configured to, by way of example only, evaluate verbal utterances, in real-time or near real-time, against one or more define algorithms or rules to identify, based upon defined criteria, an intent or criticality associated with such utterances. Based upon a determined criticality, the alert generation component 237 of the personal assistant device 228 may be configured to generate an alert indicative of or commensurate with the determined criticality. Such generated alerts then may be transmitted, for instance, to a device 216 associated with a healthcare team member 244 of the patient 242.

Continuing reference to FIG. 2, the system 200 includes a speech/text conversion component 218 communicatively coupled with the network 220. By way of example, the speech/text conversion component 218 may be configured to convert audible signals (such as the audible signal 240) into readable text and/or vice versa. The readable text may be human readable or machine readable, as appropriate. By way of example, the speech/text conversion component 218 may be configured to convert readable text into audible signals for output by the speaker 232 of the personal assistant device 228. For instance, the speech/text conversion component 218 may be configured to convert human readable text including an indication of a response to a patient request for information into audible signals for audibly providing the same to the user via the speaker 232 of the personal assistant device 228. Additionally, the speech/text conversion component 218 may be configured to convert audible signals, e.g., the audible signal 240, into text, for instance, for storage in association with the EHIS 214, for instance, in association with a patient's 242 electronic clinical records.

The system 200 additionally includes a complex language understanding (CLU) 219 component coupled with the network 220. The CLU 219 may be configured for facilitating complex language-related tasks, for instance, determining an intent and/or a criticality associated with a verbal utterance. Such CLU 219 may be integral to the system 200 or may be provided as a third-party service in accordance with aspects of the present disclosure.

Figure 3:
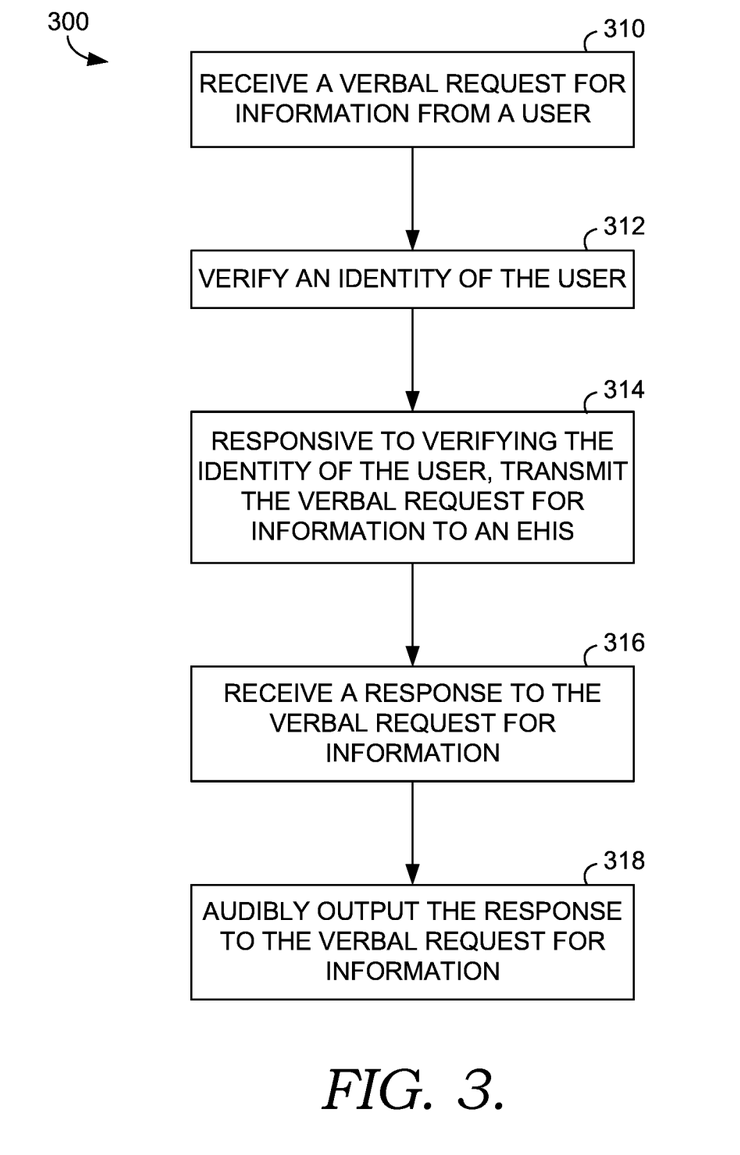
FIG. 3 is a block diagram of an exemplary method for responding to requests for information in a healthcare facility, in accordance with embodiments of the present disclosure.

With reference now to FIG. 3, a block diagram is illustrated of an exemplary method 300 for responding to requests for information in a healthcare facility. As indicated at block 310, a verbal request for information may be received from a user (e.g., the patient-user 242 or the proxy 243 of the patient 242 of FIG. 2) via a listening component (e.g., the listening component 230 of FIG. 2) of a personal assistant device (e.g., the personal assistant device 228 of FIG. 2). In embodiments, the request for information may be received as an audible signal, for instance, the audible signal 240 of FIG. 2.

As indicated at block 312, an identity of the user from whom the information request was received may be verified (e.g., utilizing the user verification component 238 of the personal assistant device 228 of FIG. 2). In embodiments, the identity of the user may be verified by: (1) detecting a voice signature of a user (e.g., the patient-user 242 or the proxy 243 of the patient 242 of FIG. 2); (2) comparing the voice signature of the user to one or more voice signatures associated, in an EHIS (e.g., the EHIS 214 of FIG. 2), with the patient as belonging to the patient (e.g., the patient 242 of FIG. 2) or an authorized proxy of the patient (e.g., the proxy 243 of the patient 242 of FIG. 2); and (3) determining the voice signature belongs to the patient (e.g., the patient 242 of FIG. 2) or the authorized proxy of the patient (e.g., the proxy 243 of the patient of FIG. 2). In embodiments, the identity of the user additionally or alternatively may be verified by comparing one or more of a location of the personal assistant device associated with the patient, a personal identification number associated with the user, a password associated with the user, a biometric-recognition profile of the user, a location of the user received from a device associated with the user and enabled with a real-time location system, and an identification credential associated with the user to information associated with the patient in an electronic healthcare information system (e.g., the EHIS 214 of FIG. 2).

As indicated at block 314, responsive to verifying the identity of the user, the received verbal information request may be transmitted (e.g., via the network 220 of FIG. 2) to an EHIS (e.g., the EHIS 214 of FIG. 2). As indicated at block 316, a response to the verbal information request may be received (e.g., by the personal assistant device 228 of FIG. 2) from the EHIS (e.g., the EHIS 214 of FIG. 2). In embodiments, it may be determined (e.g., via the content verification component 239 of the personal assistant device 228 of FIG. 2) that the response to the verbal request for information contains PHI associated with the patient (e.g., the patient 242 of FIG. 2). In such embodiments, responsive to determining the response contains PHI, it may be determined (e.g., utilizing the camera 248 of FIG. 2) if any persons other than the patient are in proximity to the personal assistance device (e.g., the personal assistant device 228 of FIG. 2). In some cases, a person may be determined to be in proximity to the personal assistant device if such person likely would be able to hear information audibly output from the speaker (e.g., the speaker 232 of FIG. 2) associated with such device (e.g., the personal assistant device 228 of FIG. 2). In some cases, a person may be determined to be in proximity to the personal assistant device if such person is within a field-of-view of a camera (e.g., the camera 248 of FIG. 2) associated with the location of the personal assistant device (e.g., the personal assistant device 228 of FIG. 2). Any and all such variations, and any combination thereof, are contemplated to be within the scope of embodiments of the present disclosure.

In embodiments, responsive to determining that at least one person other than the patient is in proximity to the personal assistant device, the identity of the at least one person may be verified (e.g., via the user verification component 238 of the personal assistant device 228 of FIG. 2) as an individual authorized to receive the PHI. In embodiments, the identity of the at least one person may be verified by comparing one or more of a voice signature of the at least one person, a personal identification number associated with the at least one person, a password associated with the at least one person, a biometric-recognition profile of the at least one person, a location of the at least one person received from a device associated with the at least one person and enabled with a real-time location system, and an identification credential associated with the at least one person to information associated with the patient in the electronic healthcare information system (e.g., the EHIS 214 of FIG. 2).

In embodiments, upon determining that the response to the received verbal request for information contains PHI, it may be determined (e.g., via the security component 241 of the personal assistant device 228 of FIG. 2) that a location of the personal assistant device is secure. In embodiments, a location of the personal assistant device may be determined to be secure if all doors and windows to the outside of the location are closed.

As indicated at block 318, the response to the verbal information request may be audibly output (e.g., via a speaker associated with the personal assistant device, for instance, the speaker 232 of the personal assistant device 228 of FIG. 2). In embodiments, the response to the verbal information request may be audibly output as an audible signal, for instance, the audible signal 240 of FIG. 2.

Figure 4:
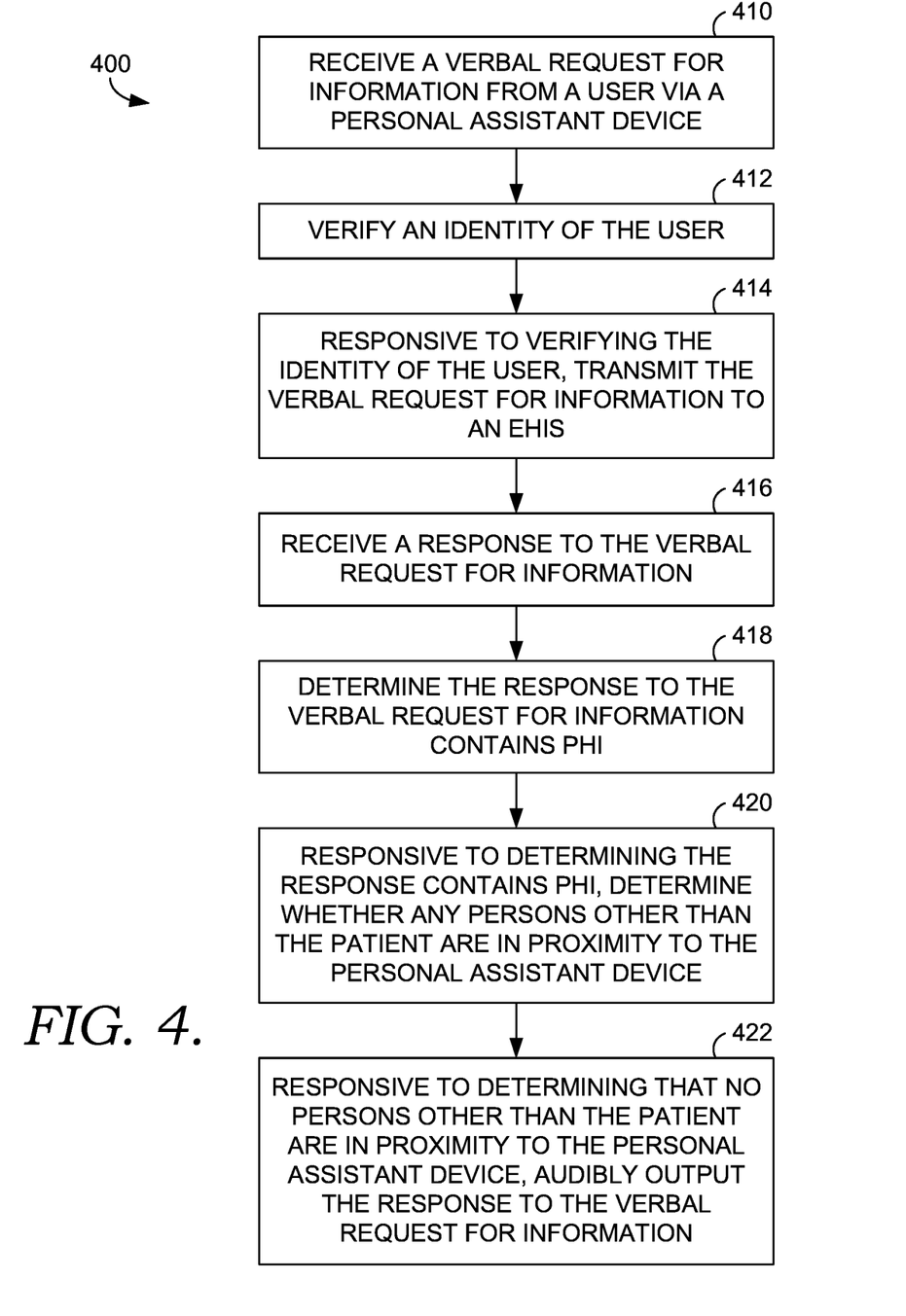
FIG. 4 is a block diagram of an exemplary method for responding to requests for information in a healthcare facility, in accordance with embodiments of the present disclosure.

Turning to FIG. 4, a block diagram is illustrated of an exemplary method 400 for responding to requests for information in a healthcare facility. As indicated at block 410, a verbal request for information may be received from a user (e.g., the patient-user 242 or the proxy 243 of the patient 242 of FIG. 2) via a listening component (e.g., the listening component 230 of FIG. 2) of a personal assistant device (e.g., the personal assistant device 228 of FIG. 2). In embodiments, the verbal request for information may be received as an audible signal, for instance, the audible signal 240 of FIG. 2.

As indicated at block 412, an identity of the user from whom the verbal request for information was received may be verified (e.g., utilizing the user verification component 238 of the personal assistant device 228 of FIG. 2). In embodiments, the identity of the user may be verified by: (1) detecting a voice signature of a user (e.g., the patient-user 242 or the proxy 243 of the patient 242 of FIG. 2); (2) comparing the voice signature of the user to one or more voice signatures associated, in an EHIS (e.g., the EHIS 214 of FIG. 2), with the patient as belonging to the patient (e.g., the patient 242 of FIG. 2) or an authorized proxy of the patient (e.g., the proxy 243 of the patient 242 of FIG. 2); and (3) determining the voice signature belongs to the patient (e.g., the patient 242 of FIG. 2) or the authorized proxy of the patient (e.g., the proxy 243 of the patient 242 of FIG. 2). In embodiments, the identity of the user may be verified, additionally or alternatively, by comparing one or more of a location of the personal assistant device (e.g., the personal assistant device 228 of FIG. 2) associated with the patient (e.g., the patient 242 of FIG. 2), a personal identification number associated with the user, a password associated with the user, a biometric-recognition profile of the user, a location of the user received from a device associated with the user and enabled with a real-time location system, and an identification credential associated with the user to information associated with the patient in an electronic healthcare information system (e.g., the EHIS 214 of FIG. 2).

As indicated at block 414, responsive to verifying the identity of the user, the received verbal request for information may be transmitted (e.g., via the network 220 of FIG. 2) to an EHIS (e.g., the EHIS 214 of FIG. 2). As indicated at block 416, a response to the verbal request for information may be received (e.g., via the personal assistant device 228 of FIG. 2). As indicated at block 418, it may be determined (e.g., via the content verification component 239 of the personal assistant device 228 of FIG. 2) that the response to the verbal information request contains protected health information associated with the patient.

As indicated at block 420, responsive to determining that the response to the verbal information request contains PHI, it may be determined (for instance, utilizing the camera 248 of FIG. 2) if any persons other than the patient are in proximity to the personal assistant device. In some cases, a person may be determined to be in proximity to the personal assistant device if such person likely would be able to hear information audibly output from the speaker (e.g., the speaker 232 of FIG. 2) associated with such device (e.g., the personal assistant device 228 of FIG. 2). In some cases, a person may be determined to be in proximity to the personal assistant device if such person is within the field-of-view of a camera (e.g., the camera 248 of FIG. 2) associated with the location of the personal assistant device (e.g., the personal assistant device 228 of FIG. 2). Any and all such variations, and any combination thereof, are contemplated to be within the scope of embodiments of the present disclosure.

In embodiments, responsive to determining that at least one person other than the patient is in proximity to the personal assistant device, an alternate response to the response to the request for information may be audibly output, that is, an alternate response that does not contain PHI of the patient. In embodiments, the alternate response may be output as an audible signal, for instance, the audible signal 240 of FIG. 2. In embodiments, responsive to determining that at least one person other than the patient is in proximity to the personal assistant device, a textual response to the verbal request for information may be output in association with a device that is associated with the patient and that is not the personal assistant device (e.g., the mobile phone 222, the user computing device 224, and/or the wearable device 226 of FIG. 2). In embodiments, prior to outputting such textual response, the response to the verbal request for information may be converted to text, e.g., via the speech/text conversion component 218 of FIG. 2.

In embodiments, responsive to determining that at least one person other than the patient is in proximity to the personal assistant device (e.g., the personal assistant device 228 of FIG. 2), an identity of the at least one person may be verified as an individual authorized to receive the PHI. In embodiments, the identity of the at least one person other than the patient as an individual authorized to receive the PHI may be verified by comparing one or more of a voice signature of the at least one person, a personal identification number associated with the at least one person, a password associated with the at least one person, a biometric-recognition profile of the at least one person, a location of the at least one person received from a device associated with the at least one person and enabled with a real-time location system, and an identification credential associated with the at least one person to information associated with the patient in the electronic healthcare information system (e.g., the EHIS 214 of FIG. 2).

As indicated at block 422, responsive to determining that no persons other than the patient are in proximity to the personal assistant device (or upon verifying the identity of a person other than the patient in proximity to the personal assistant device as an individual authorized to receive the PHI), the response to the verbal request for information may be audibly output, for instance, via the speaker 232 of the personal assistant device 228 of FIG. 2. In embodiments, the response to the verbal request for information may be output as an audible signal, for instance, the audible signal 240 of FIG. 2.

In embodiments, upon determining that the response to the received verbal request for information contains PHI, it may be determined (e.g., via the security component 241 of the personal assistant device 228 of FIG. 2) that a location of the personal assistant device is secure. In embodiments, a location of the personal assistant device may be determined to be secure if all doors and windows to the outside of the location are closed. Responsive to determining that the location of the personal assistant device is secure, the response to the received verbal information request may be audibly output, e.g., via the speaker 232 of the personal assistant device 228 of FIG. 2. In embodiments, the response to the received verbal information request may be output as an audible signal, for instance, the audible signal 240 of FIG. 2.

Figure 5:
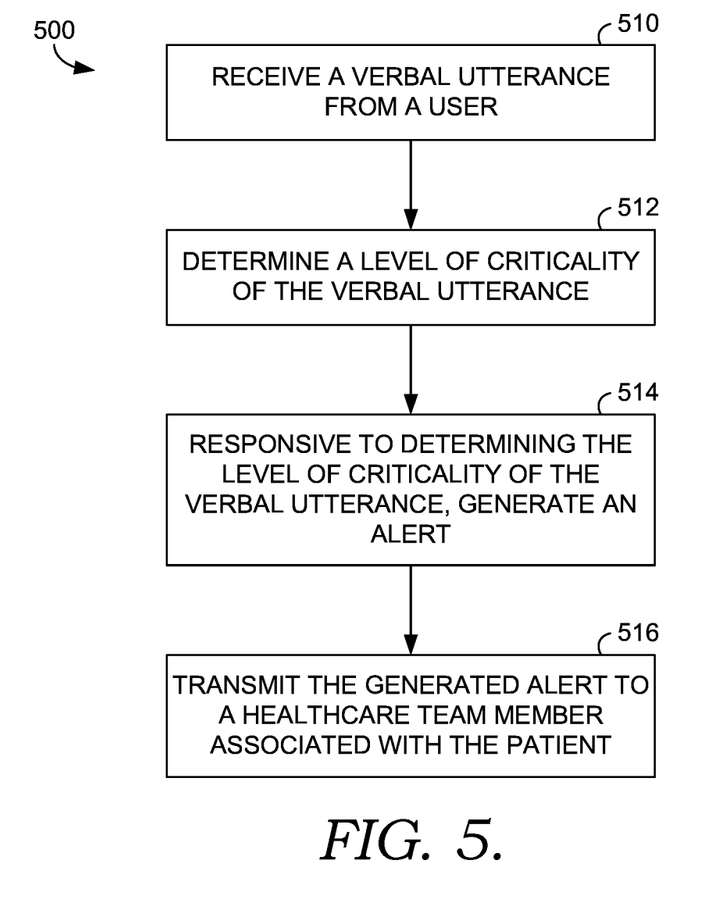
FIG. 5 is a block diagram of an exemplary method for generating alerts responsive to verbal utterances in a healthcare facility, in accordance with embodiments of the present disclosure.

With reference to FIG. 5, a block diagram is illustrated of an exemplary method 500 for generating alerts responsive to verbal utterances in a healthcare facility. As indicated at block 510, a verbal utterance may be received from a user, for instance, a patient-user (e.g., the patient 242 of FIG. 2) or a proxy of a patient (e.g., the proxy 243 of the patient 242 of FIG. 2) via a listening component (e.g., the listening component 230) of a personal assistant device (e.g., the personal assistant device 228 of FIG. 2) associated with a location of a patient (e.g., the patient 242) in the healthcare facility. In embodiments, the verbal utterance may be received as an audible signal, for instance, the audible signal 240 of FIG. 2. In embodiments, the personal assistant device may be configured to receive verbal utterances from the user (e.g., via the listening component 230 of the personal assistant device 228 of FIG. 2) and to audibly provide responses to received verbal utterances (e.g., via the speaker 232 of the personal assistant device 228 of FIG. 2).

As indicated at block 512, a level of criticality of the verbal utterance may be determined (e.g., via the alert generation component 238 of the personal assistant device 228 of FIG. 2). In embodiments, the level of criticality may be determined utilizing one or more of words contained in the received verbal utterance, phrases contained in the received verbal utterance, intonation of the received verbal utterance, a facial expression of the user when speaking the received verbal utterance, and a gesture of the user when speaking the received verbal utterance.

As indicated at block 514, responsive to determining the level of criticality of the verbal utterance, an alert may be generated (e.g., by the alert generation component 237 of the personal assistant device 228 of FIG. 2). In embodiments, the level of criticality of the generated alert may be indicative of or commensurate with the determined level of criticality of the verbal utterance. As indicated at block 516, the generated alert may be transmitted (e.g., via the network 220 of FIG. 2) to at least one member of a healthcare team associated with the patient (e.g., the healthcare team member 244 of FIG. 2).

From the foregoing, it will be seen that this technology is one well adapted to attain all the ends and objects described, and together with other advantages which are obvious and inherent to the structure. It will be understood that certain features and sub-combinations are of utility and may be employed without reference to other features and subcombinations. This is contemplated by and is within the scope of the claims. Since many possible embodiments may be made of the present technology without departing from the scope, it is to be understood that all matter described or shown in the accompanying drawings is to be interpreted as illustrative and not in a limiting sense.

What is claimed is:

1. A system for responding to requests for information in a healthcare facility, the system comprising:
a personal assistant device associated with a location of a patient in the healthcare facility and having a listening component and a speaker, the personal assistant device being configured to receive verbal requests for information from a user and to audibly provide responses to received verbal requests;
a processor in communication with the personal assistant device and an electronic healthcare information system; and
one or more computer-readable media storing computer-readable instructions that, when executed by the processor, cause the processor to:
receive, via the listening component, a verbal request for information from the user;
verify an identity of the user;
responsive to verifying the identity of the user, transmit the received verbal request for information to the electronic healthcare information system;
receive, from the electronic healthcare information system, a response to the verbal request for information;
determine that the response to the verbal request for information contains protected health information; and
responsive to determining that the response to the verbal request for information contains the protected health information, determine no persons other than the patient are in the field of view of a camera that is in proximity to the personal assistant device prior to audibly outputting the response to the verbal request for information; and
audibly output, via the speaker, the response to the verbal request for information.

2. The system of claim 1, wherein the user is one of the patient and a proxy of the patient.

3. The system of claim 1, wherein the one or more computer-readable media storing computer-readable instructions, when executed by the processor, cause the processor to verify the identity of the user by:
detecting a voice signature of the user based upon the received verbal request for information;
comparing the detected voice signature of the user to one or more voice signatures associated, in the electronic healthcare information system, with the patient as belonging to the patient or an authorized proxy of the patient; and
determining the voice signature belongs to the patient or the authorized proxy of the patient.

4. The system of claim 3, wherein the one or more computer-readable media storing computer-readable instructions, when executed by the processor, cause the processor to further verify the identity of the user by comparing one or more of a location of the personal assistant device associated with the patient, a personal identification number associated with the user, a password associated with the user, a biometric-recognition profile of the user, a location of the user received from a device associated with the user and enabled with a real-time location system, and input of an identification credential associated with the user to information associated with the patient in the electronic healthcare information system.

5. The system of claim 4, wherein upon determining that at least one person other than the patient is in proximity to the personal assistant device, the one or more computer-readable media storing computer-readable instructions, when executed by the processor, cause the processor to verify an identity of the at least one person other than the patient as an individual authorized to receive the protected health information prior to audibly outputting the response to the verbal request for information.

6. The system of claim 5, wherein the one or more computer-readable media storing computer-readable instructions, when executed by the processor, cause the processor to verify the identity of the at least one person other than the patient by comparing one or more of a voice signature of the at least one person, a personal identification number associated with the at least one person, a password associated with the at least one person, a biometric-recognition profile of the at least one person, a location of the at least one person received from a device associated with the at least one person and enabled with a real-time location system, and input of an identification credential associated with the at least one person to information associated with the patient in the electronic healthcare information system.

7. The system of claim 1, wherein the one or more computer-readable media storing computer-readable instructions, when executed by the processor, further cause the processor to:
determine that the response to the verbal request for information contains protected health information; and
determine that the location of the personal assistant device is secure prior to audibly outputting the response to the verbal request for information.

8. The system of claim 1, wherein at least one of the received verbal request for information and the received response to the verbal request for information is stored in the electronic healthcare information system and associated with the patient.

9. A system for responding to requests for information in a healthcare facility, the system comprising:
a personal assistant device associated with a location of a patient in the healthcare facility and having a listening component and a speaker, the personal assistant device being configured to receive verbal requests for information from a user and to audibly provide responses to received verbal requests for information;
a processor in communication with the personal assistant device and an electronic healthcare information system; and
one or more computer-readable media storing computer-readable instructions that, when executed by the processor, cause the processor to:
receive, via the listening component, a verbal request for information from the user;
verify an identity of the user;
responsive to verifying the identity of the user, transmit the received verbal request for information to the electronic healthcare information system;
receive, from the electronic healthcare information system, a response to the verbal request for information;
determine that the response to the verbal request for information contains protected health information; and responsive to determining that the response to the verbal request for information contains the protected health information, determine no persons other than the patient are in the field of view of a camera that is in proximity to the personal assistant device; and responsive to determining that no persons other than the patient are in proximity to the personal assistant device, audibly output, via the speaker, the response to the verbal request for information.

10. The system of claim 9, wherein the user is one of the patient and a proxy of the patient.

11. The system of claim 9, wherein responsive to determining that at least one person other than the patient is in proximity to the personal assistant device, the one or more computer-readable media storing computer-readable instructions, when executed by the processor, cause the processor to audibly output an alternate response to the verbal request for information that does not contain personal health information.

12. The system of claim 9, wherein responsive to determining that at least one person other than the patient is in proximity to the personal assistant device, the one or more computer-readable media storing computer-readable instructions, when executed by the processor, cause the processor to output a textual response to the verbal request for information in association with a device that is associated with the patient other than the personal assistant device.

13. The system of claim 9, wherein responsive to determining that at least one person other than the patient is in proximity to the personal assistant device, the one or more computer-readable media storing computer-readable instructions, when executed by the processor, cause the processor to:

verify an identity of the at least one person other than the patient as an individual authorized to receive the protected health information; and responsive to verifying the identity of the at least one person other than the patient as an individual authorized to receive the protected health information, audibly output, via the speaker, the response to the verbal request for information.

14. The system of claim 13, wherein the one or more computer-readable media storing computer-readable instructions, when executed by the processor, cause the processor to verify the identity of the at least one person other than the patient as an individual authorized to receive the protected health information by comparing one or more of a voice signature of the at least one person, a personal identification number associated with the at least one person, a password associated with the at least one person, a biometric-recognition profile of the at least one person, a location of the at least one person received from a device associated with the at least one person and enabled with a real-time location system, and input of an identification credential associated with the at least one person to information associated with the patient in the electronic healthcare information system.

15. The system of claim 9, wherein the one or more computer-readable media storing computer-readable instructions, when executed by the processor, further cause the processor to:

determine that the location of the patient is secure prior to audibly outputting the response to the verbal request for information; and responsive to determining that the location of the patient is secure, audibly output, via the speaker, the response to the verbal request for information.

16. The system of claim 9, wherein at least one of the received verbal request for information and the received response to the verbal request for information is stored in the electronic healthcare information system and associated with the patient.

* * * * *